United States Patent [19]

Saville

[11] Patent Number: Plant 5,482

[45] Date of Patent: Jun. 4, 1985

[54] ROSE PLANT

[75] Inventor: F. Harmon Saville, Rowley, Mass.

[73] Assignee: Nor'East Miniature Roses, Inc., Rowley, Mass.

[21] Appl. No.: 556,267

[22] Filed: Nov. 30, 1983

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new lemon yellow and currant red multi-color miniature rose variety of good exhibition form.

1 Drawing Figure

1

The present invention relates to a new and distinct variety of rose plant of the miniature rose class, which was originated by my crossing as seed parent the rose known as "Rise 'N Shine" (U.S. Plant Pat. No. 4,231) and the rose known as "Watercolor" (U.S. Plant Pat. No. 4,031) as pollen parent. The varietal denomination of this new variety is "Savalife".

Among the novel characteristics possessed by this new variety which distinguish it from its parents and all other varieties of which I am aware are its unusual lemon yellow and currant red flowers of exhibition form with good to heavy petalage which maintain good form until fully open and which are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "6A" is plate 6A of The Royal Horticultural Society Colour Chart.

Parentage: Seedling.

*Seed parent.*—"Rise 'N Shine".

*Pollen parent.*—"Watercolor".

Class: Miniature.

The following observations are made of specimens grown outdoors in Essex County, Mass., during the month of October.

FLOWER

Blooming habit: Near continuous.

Bud:

(1) *Size.*—Medium.

(2) *Form.*—Long pointed.

(3) *Color.*—When sepals first divide — Sulfur yellow 6A flushed with Jasper red 39A. When petals begin to unfurl — near Dresden yellow 5B flushed with 39A to orange red 34A.

(4) *Sepals.*—Longer than bud, slightly foliated.

2

(5) *Peduncle.*—Length — about $\frac{3}{4}$ inch. Aspect — straight. Strength — erect. Color — near 148C.

Bloom:

(1) *Size.*—Average size when fully expanded — about $1\frac{1}{4}$ to $1\frac{3}{4}$ inches.

(2) *Borne.*—Singly and sprays.

(3) *Form.*—High centered through $\frac{3}{4}$ open stage, becoming flat, petals reflex sharply upon opening; flower maintains symmetrical exhibition form.

(4) *Petalage.*—Number of petals under normal conditions — about 30 to 36.

(5) *Color.*—After sepals fall and sulfur yellow buds with Jasper red flush begin to unfurl, yellow coloring becomes lemon yellow 13A and continues to predominate. However, becoming more visible as flowers open is currant red coloring 47A through 47D seen on the petal edges of the outer petals on the petal top surface. The red coloring appears more concentrated at the outer petal edge and washes through a narrow zone into the main lemon yellow coloring of the remainder of the petal giving the impression of an abrupt color change. The red tones are only occasionally seen on inner petals and then only at the petal apices and edges. The general tonality is a lemon yellow flower coloring with red-edged outer petals. As flowers open further past exhibition stage, red coloring becomes less visible being seen essentially only at the petal apices on sharply reflexed outer petals.

Petals:

(1) *Texture.*—Thick.

(2) *Appearance.*—Inside — satiny, outside — matte.

(3) *Form.*—Wide oval, fan shaped.

(4) *Arrangement.*—Regularly arranged, shingle-like.

(5) *Petaloids in center.*—Few.

(6) *Persistence.*—Drop off cleanly.

(7) *Fragrance.*—None.

(8) *Lasting quality.*—Long lasting on plant and very long lasting as cut flower.

REPRODUCTIVE ORGANS

Stamens, filaments and anthers:

(1) *Arrangement.*—Regularly arranged around styles.

(2) *Color.*—Near 22A.

Pollen:

*Color.*—Near 22A.

Styles: Even, medium length.
Stigmas:
*Color.*—Near 160B.
Hips:
*Shape.*—Globular.
*Size.*—About $\frac{5}{8}$ inch.
*Color.*—Orange red.
*Do seeds protrude?*—No.

PLANT

Form: Bushy, compact.
Growth: Very vigorous, uniform branching.
*Height attained.*—About 12 to 18 inches.
Foliage: Compound 5 to 7 leaflets.
(1) *Size.*—Medium.
(2) *Quantity.*—Abundant.
(3) *Color.*—New foliage: Upper side — near to 146A. Under side — near to 146C. Old foliage: Upper side — near 133A. Under side — near 191A.
(4) *Shape.*—Oval.
(5) *Texture.*—Upper side is glossy and under side is matte.
(6) *Edge.*—Serrated.
(7) *Serration.*—Serrulate.
(8) *Leaf stem.*—Color — near to 138A. Under side — near 144A.

(9) *Stipules.*—Medium.
(10) *Resistance to disease.*—Blackspot — average. Mildew — average. Rust — average.
Wood:
(1) *New wood.*—Color — near 60B. Bark — smooth.
(2) *Old wood.*—Color — near 137C. Bark — smooth.
Thorns:
(1) *Thorns.*—Quantity (main stalk): ordinary. On laterals from stalk — few. Form — long, thin, pointed, angled slightly downward. Length — medium. Color — near 60B. Position — irregular.
(2) Prickles.—Few.
Winter hardiness: Requires ordinary protection in extreme climates.

I claim:

1. A new and distinct variety of rose plant of the miniature rose class, substantially as shown and described, characterized particularly by bright lemon yellow and currant red flowers of good exhibition form and medium to heavy petalage with petals reflexing upon opening displaying red toned outer petal edges and apices and retaining good exhibition form until open.

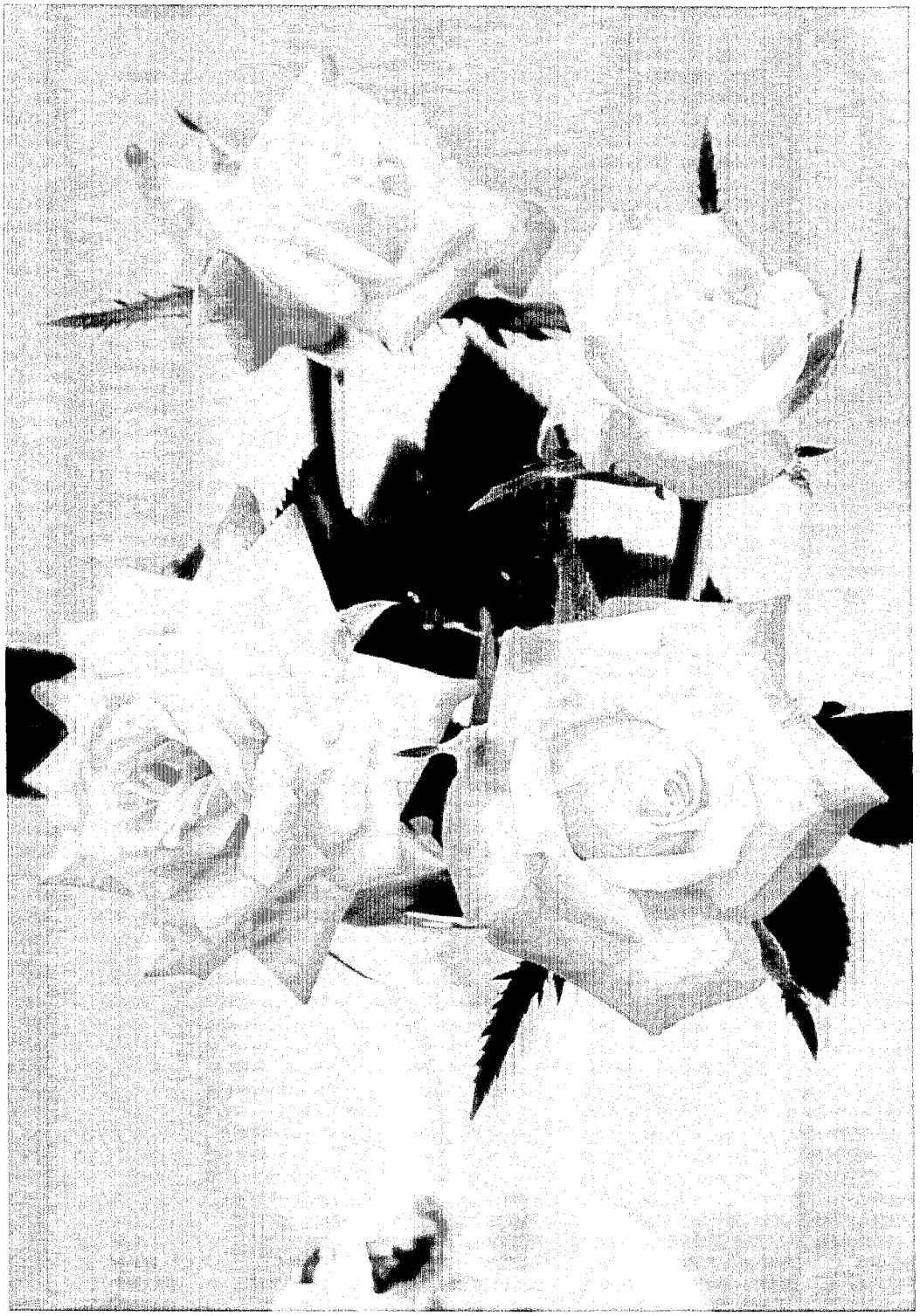

* * * * *